(12) United States Patent
Forster et al.

(10) Patent No.: US 6,276,936 B1
(45) Date of Patent: Aug. 21, 2001

(54) DENTAL SEPARATOR FOR SOLIDS FROM A SOLIDS/LIQUID MIXTURE

(76) Inventors: Michael Forster, Bichlweg 5, A-6112 Wattens; Bruno Pregenzer, Untermieming 45a, A-6414 Mieming; Alfred Konzett, Dorfstrasse 21a, A-6082 Patsch, all of (AT)

( * ) Notice: Subject to any disclaimer, the term of this patent is extended or adjusted under 35 U.S.C. 154(b) by 0 days.

(21) Appl. No.: 09/408,680

(22) Filed: Sep. 30, 1999

(51) Int. Cl.[7] .................................................. B01D 21/00
(52) U.S. Cl. ............................ 433/92; 210/305; 210/521
(58) Field of Search ............................. 433/92; 210/320, 210/521, 305, 311

(56) References Cited

U.S. PATENT DOCUMENTS

| | | | |
|---|---|---|---|
| 1,172,202 | * | 2/1916 | Flood ..................................... 433/92 |
| 3,777,403 | | 12/1973 | Ritchie . |
| 4,328,101 | * | 5/1982 | Broden .................................. 433/92 |
| 4,356,959 | * | 11/1982 | Rosander ............................... 433/92 |
| 4,580,978 | * | 4/1986 | Motola et al. ......................... 433/92 |
| 4,591,437 | * | 5/1986 | Ernryd et al. .......................... 433/92 |
| 4,842,478 | * | 6/1989 | Durr et al. ............................. 433/92 |
| 4,919,826 | * | 4/1990 | Alzner ................................... 433/92 |
| 5,017,135 | * | 5/1991 | Meyer ................................... 433/92 |
| 5,018,971 | | 5/1991 | Trawöger et al. . |
| 5,613,851 | | 3/1997 | Trawöger et al. . |
| 6,083,391 | * | 7/2000 | Pregenzer et al. .................... 210/305 |

FOREIGN PATENT DOCUMENTS

| | | |
|---|---|---|
| 401 228 | 7/1996 | (AT) . |
| 34 17 248 A1 | 11/1985 | (DE) . |
| 3813264 | * 11/1998 | (DE) ..................................... 433/92 |

OTHER PUBLICATIONS

International Publication WO 98/46324 (Ernryd), dated Oct. 22, 1998.

* cited by examiner

*Primary Examiner*—Ralph A. Lewis
(74) *Attorney, Agent, or Firm*—Herbert L. Lerner; Laurence A. Greenber; Werner H. Stemer

(57) ABSTRACT

For separating off solids from a solid/liquid mixture occurring in a dental treatment station, a housing has a sedimentation tank, in which two sedimentation zones are disposed one above the other. Both the mixture inlet and the liquid outlet are disposed above a predetermined sedimentation height, and the liquid outlet is provided on a tube that leads through the sedimentation tank into an outlet chamber disposed below it.

13 Claims, 4 Drawing Sheets

DENTAL SEPARATOR FOR SOLIDS FROM A SOLIDS/LIQUID MIXTURE

BACKGROUND OF THE INVENTION

Field of the Invention

The invention relates to a dental separator. Such separators are used for separating solids from a solid/liquid mixture that result in a dental treatment station upon being aspirated from the mouth of the patient. The solids include drilling dust, bone splinters, mercury-amalgam particles, and possibly also particles of dental metals such as dental gold, and so forth; the mercury, above all, must not reach the wastewater, for the sake of environmental protection.

For about twenty years, at least a substantial portion of the solids has therefore been separated out of the mixture; three fundamentally different options are available for this, namely settling heavy particles out by the influence of gravity, settling with active reinforcement by centrifugal forces in centrifugal drums or the like, and trapping particles over a certain size by means of filters, screens or the like. Examples are found for instance in U.S. Pat. Nos. 5,018,971 and 5,613,851.

Each of these three options has disadvantages: Trapping solids with filters and screens inserted into the flow means that the pores and mesh become stopped up rapidly; settling by gravity demands a slow flow through the solid separation chamber, with as little impediment as possible, which is difficult to achieve in dentistry because the inflow rate fluctuates greatly; and separation by means of centrifuges requires much more complex equipment, with a drive motor, controls, and so forth.

SUMMARY OF THE INVENTION

One object of the invention is to improve the separation out of solids by gravity from a dental solid/liquid mixture in a compact separator, in which it should be possible to process flow rates of six to eight liters per minute.

A further object of the invention is an additional separating out of aspirated air that entrains the solid/liquid mixture, before the mixture enters the solid separation chamber, resulting in three-phase separation.

A further object of the invention is to separate out solids from an aspirated air/solid/liquid mixture, where the aspirated air is first separated from the solid/liquid mixture, then the solids are settled out of the liquid by gravity, and finally the aspirated air and the solid-free liquid are mixed together again and delivered jointly to the suction pump.

A further object of the invention is additionally separating environmentally polluting heavy metal ions from the clarified liquid leaving the solid separation chamber.

With the above and other objects in view there is provided, in accordance with the invention, a dental separator for separating out solids from a solid/liquid mixture after aspirated air has been separated off, in a dental aspiration system, comprising:

a sedimentation tank for solids communicating fluidically with an upper inlet line and a lower wastewater conduit;

the sedimentation tank formed with a lower sedimentation zone and an upper sedimentation zone;

overflow ribs dividing the upper sedimentation zone into a plurality of chambers including a last chamber formed with a liquid outlet; and a tube communicating with the liquid outlet formed in the last chamber and extending downward through the sedimentation tank towards the wastewater conduit.

In accordance with an added feature of the invention, the upper sedimentation zone is embodied in an insert element adapted to be inserted into the sedimentation tank, the insert element being formed with first and second bottom openings diametrically opposite one another and the overflow ribs disposed as mutually parallel overflow ribs therebetween, the first bottom opening fluidically connecting the lower sedimentation zone located below and the second bottom opening receiving the tube.

In accordance with an additional feature of the invention, an annular rib surrounds the upper sedimentation zone and forms, outside thereof, a peripheral inlet chamber communicating fluidically with the lower sedimentation zone.

In accordance with another feature of the invention, there is provided an immersion wall protruding variously deeply into the lower sedimentation zone and extending over a portion of a circumference of the annular rib.

With the above objects in view there is also provided, in accordance with the invention, a dental separator for separating out solids from a solid/liquid mixture after aspirated air has been separated off in a dental aspiration system, comprising:

a housing formed with an inlet opening and a wastewater outlet;

a sedimentation tank in the housing and adapted to communicate fluidically with the inlet opening, being formed with a lower sedimentation zone and an upper sedimentation zone, and defining a predetermined sedimentation height, the lower sedimentation zone being formed with a mixture inlet above the sedimentation height and the upper sedimentation zone being formed with a liquid outlet above the sedimentation height; and an outlet chamber formed in the housing below the sedimentation tank and adapted to communicate fluidically with the wastewater conduit; and a tube fluidically connecting the liquid outlet of the sedimentation tank to the outlet chamber and extending through the sedimentation tank into the outlet chamber.

In other words, the objects are satisfied with a separator according to the invention, which is provided with a sedimentation tank for the solids, which can be made to communicate fluidically with an upper inlet line and a lower wastewater conduit, and in which a first lower and a second upper sedimentation zone are formed; the second sedimentation zone has at least two chambers, separated from one another by overflow ribs, in the latter of which chambers a liquid outlet is provided, from which a tube which can be made to communicate with the wastewater conduit is extended downward, through the sedimentation tank. Disposing the two sedimentation zones one above the other assures adequately good sedimentation conditions in a small space, even if the flow rates fluctuate greatly. Because the mixture inlet and the liquid outlet are located at the top, the sedimentation tank is flooded, and there is a vertical flow reversal.

The mixture arriving via the inlet line preferably flows through the annular inlet chamber outside the second, upper sedimentation zone, downward into the first, lower sedimentation zone, where it is deflected inward and upward. The inlet chamber, whose width is slight, contributes substantially to the calm in the solid separation chamber, because turbulence from the inlet chamber can hardly reach the interior of the sedimentation tank.

The annular inlet chamber is lengthened at the bottom by an immersion wall, so that the flow reversal is dictated by the lower edge of the immersion wall. The lower edge of the immersion wall extends not horizontally but instead ascends to both sides from a lowermost region under the mixture inlet. The course of the lower edge of the immersion wall is selected such that the spacing between the mixture inlet and the edge is at least the same at every point. At the beginning of separation operation, a flow becomes established in which away from the mixture inlet a vertical downward component predominates, until the material settling out blocks up this preferred flow path on its own. The flow shifts as a result and increasingly gains a peripheral component along the immersion wall. As a result, not only is the sedimentation height raised to a level that is substantially above the lowermost region of the immersion wall, so that not only is a very large holding capacity of the sedimentation tank attained, but also the sedimentation time is not merely maintained, but even increased.

To enable even dissolved mercury compounds to be removed from the liquid, an inlay, for instance of activated charcoal, that binds mercury and/or mercury ions can be associated with the transition between the two sedimentation zones.

With the above and other objects in view there is also provided, in accordance with the invention, a dental aspiration system having a suction nozzle aspirating an air/solid/liquid mixture from a patient's mouth and a pump communicating with the suction nozzle via a suction line having a first portion and a second portion, and a dental separator for separating the air/solid/liquid mixture connected to the suction nozzle via the first portion of the suction line and to the pump via the second portion of the suction line. The air/solid/liquid separator comprises:

a housing formed with an air separation chamber adapted to communicate fluidically with the first portion of the suction line and having deflection faces, the air separation chamber and which has an air outlet and an outlet for the solid/liquid mixture;

a sedimentation tank for solids disposed below the air separation chamber and communicating fluidically with the outlet for the solid/liquid mixture, the sedimentation tank being formed with a liquid outlet above a predetermined sedimentation height;

an outlet chamber adapted to communicate fluidically with the second portion of the suction line and being disposed below the sedimentation tank; and the air outlet of the air separation chamber and the liquid outlet of the sedimentation tank communicating with the outlet chamber via a tube extending through the sedimentation tank and into the outlet chamber.

In this further preferred embodiment, the entraining aspirated air is separated from the mixture in an air separation chamber embodied in the housing above the sedimentation tank; in this chamber, the air is guided over deflection faces and aspirated away through an air outlet. In this embodiment, the liquid, which is practically free of environmentally polluting substances, can not merely be carried into the wastewater conduit but can even be added to the aspirated air again, if a water ring pump, for instance, that requires sealing fluid is used as the suction pump. The cleaned liquid in this case is aspirated back into the airflow in an outlet chamber disposed below the sedimentation tank and is carried away by this flow.

In accordance with again an added feature of the invention, the air outlet and the liquid outlet are each provided via a respective tube discharging freely into the outlet chamber. In a preferred embodiment, the two tubes extend parallel to one another, and the tube of the air outlet is disposed centrally in the sedimentation tank, and the tube of the liquid outlet is disposed along a side wall of the sedimentation tank.

In accordance with again an additional feature of the invention, the housing comprises a lower part, a middle part, and an upper part, the sedimentation tank forming the middle part detachably joined to the upper part surrounding the air separation chamber and to the lower part formed by the outlet chamber.

In accordance with again another feature of the invention, the second sedimentation zone is embodied in an insert element adapted to be inserted into the sedimentation tank and formed with first, second, and third bottom openings and mutually parallel overflow ribs, the second bottom opening being disposed diametrically opposite the first bottom opening and receiving the tube of the liquid outlet, and the tube of the air outlet extending through the third, central bottom opening.

In accordance with again a further feature of the invention, laminations ascending crosswise to an inflow direction disposed in the inlet chamber, the laminations having mutually spaced apart radial edges and being disposed one above the other.

For shielding the second sedimentation zone, the insert element preferably has an annular rib, outside which the peripheral inlet chamber into the first sedimentation zone is provided. Especially if an air separation chamber is formed, laminations ascending in the inflow direction can be provided in the inlet chamber, with their radial edges disposed one above the other in spaced-apart fashion. The inlet chamber is thereby divided into a number of slot-like passages between the laminations, which slow down the inflowing mixture.

The second sedimentation zone embodied in particular in the insert element, in a further preferred embodiment, includes at least two chambers separated from one another by overflow ribs, in the latter of which chambers the liquid outlet is provided.

Other features which are considered as characteristic for the invention are set forth in the appended claims.

Although the invention is illustrated and described herein as embodied in a dental separator, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
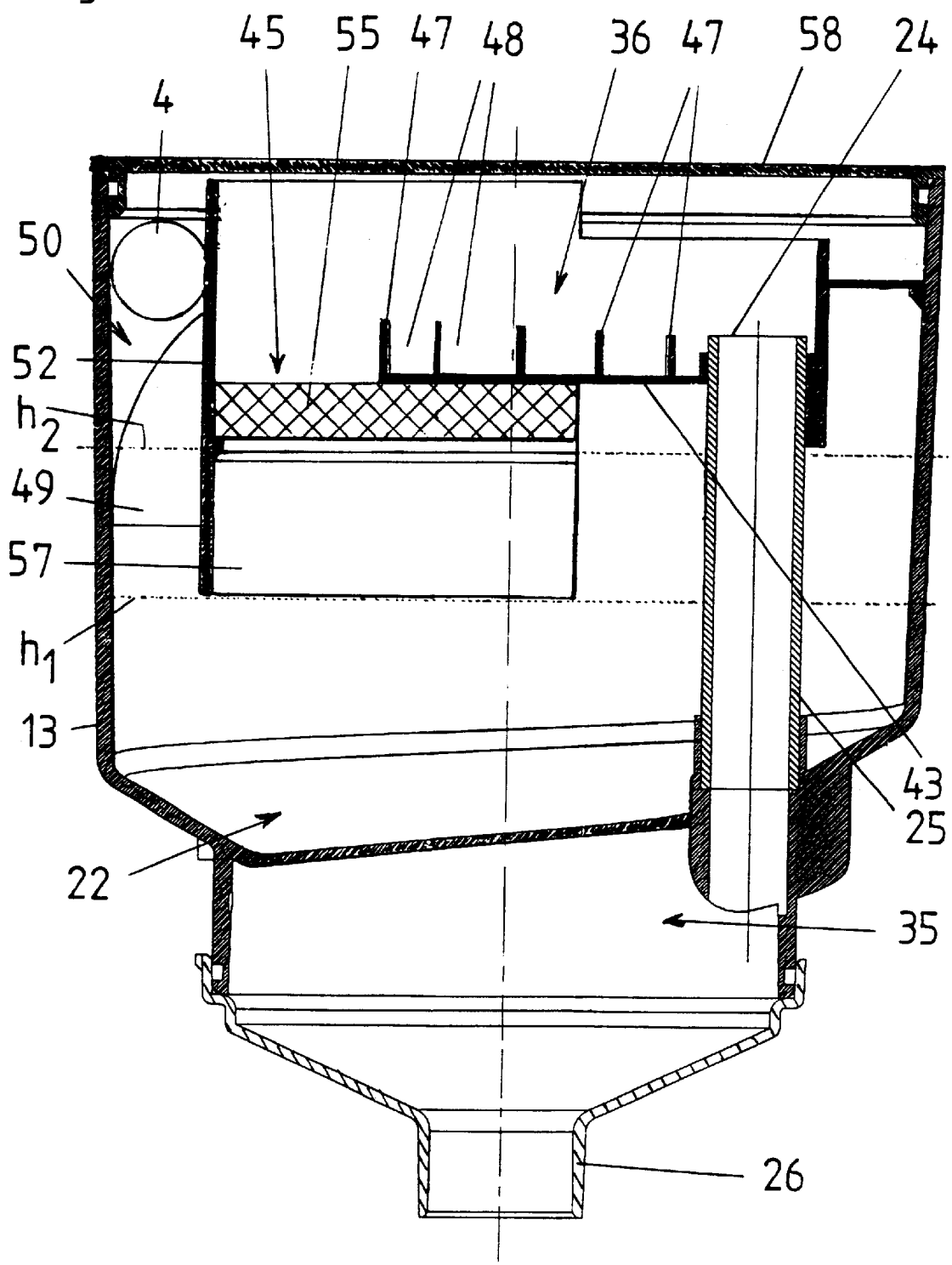
FIG. 1 is a longitudinal section through a first embodiment of the separator according to the invention.

Referring now to the figures of the drawing in detail and first, particularly, to FIG. 1 thereof, there is seen a separator for separating solids out of a liquid. The mixture aspirated from the mouth of a patient by a saliva aspirator is separated from the aspirated air in a preceding air separator and is discharged from the negative-pressure region of a dental aspiration system via a pressure sluice, a valve, or the like. Thus the separator is at normal air pressure. The mixture passes through a mixture inlet 4 into a sedimentation tank 13, which is provided with a cap 58 and whose inlet chamber 50 is partitioned off from the center region by an annular rib 52.

Below the inlet chamber 50, the sedimentation tank 13 has a first sedimentation zone 22, in which above all coarser and heavier particles collect, and through which the mixture passes from top to bottom. At the lower end of an immersion wall 57, provided in an extension of the annular rib 52 over a portion of the circumference, the flow in the liquid is deflected inward and upward into the second sedimentation zone 36, where above all fine and superfine solid particles are still being entrained. As soon as the sedimentation has reached the level $h_1$, which is predetermined by the lower edge of the immersion wall 57, the flow course described is blocked, and the flow shifts along the immersion wall 57 peripherally as far as its end, so that despite the rising sedimentation surface the flow course is not shortened. The maximum sedimentation height $h_2$ of the first sedimentation zone 22 is defined by the lower edge of the annular rib 52.

Figure 3:
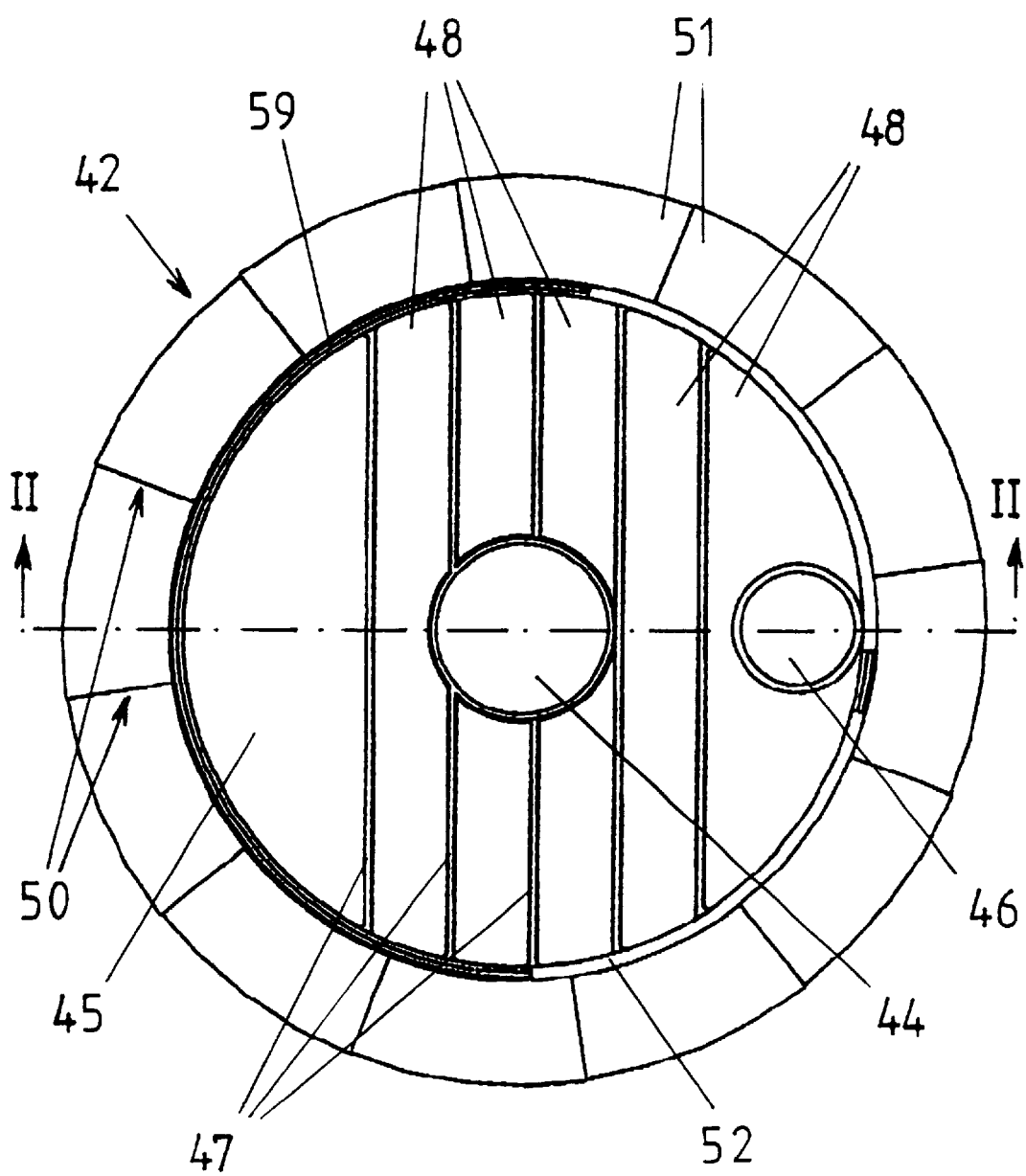
FIG. 3 is a plan view on an insert element of the sedimentation tank.

The second sedimentation zone 36 is provided in an insert element 42, which is inserted into the sedimentation tank 13 and is provided with the annular rib 52 and has a bottom 43, from which, as can be seen especially from FIG. 3, parallel overflow ribs 47 protrude upward, defining chambers 48. The bottom 43 has a first opening 45, which represents the flow communication with the first sedimentation zone 22, and in the last chamber 48 it has a second opening 46, through which a tube 25 is passed through the sedimentation tank 13 downward into an outlet chamber 35. The upper edge of the tube 25 forms the liquid outlet 24 of the sedimentation tank 13, into which, after passing through the chambers 48 of the second sedimentation zone 36, liquid flows that is now practically free of solids. The outlet chamber 35 is provided with an outlet 26, which can be connected to a wastewater line.

The mixture inlet 4 is located at the same height as, or preferably slightly higher than, the upper edge of the highest overflow rib 47, and thus the sedimentation tank 13 is filled up to this upper edge with liquid. Calming vanes 49 are additionally provided, in order as much as possible to prevent turbulence, which can impede the sedimentation, at least in the inlet chamber 50. The first opening 45 in the insert element 42 can, as FIG. 1 shows, also be covered with an inlay 55, which binds dissolved mercury ions and/or super finely dispersed mercury in elemental and/or vapor form. The inlay 56 can for instance be of spun metal, woven metal fabric, metal foam, and so forth, comprising a metal that alloys mercury or is non-noble with respect to mercury (iron, zinc, tin, magnesium, copper, etc.). For the removal of mercury ions, the inlay 55 may also have ion-exchanging properties, and can for instance include thiol, thiourea, or similar ion-exchanging materials. The inlay 55 can furthermore contain activated charcoal as well.

The outlet chamber 35 is provided with an outlet 26, which can be connected to a wastewater line.

Figure 2:
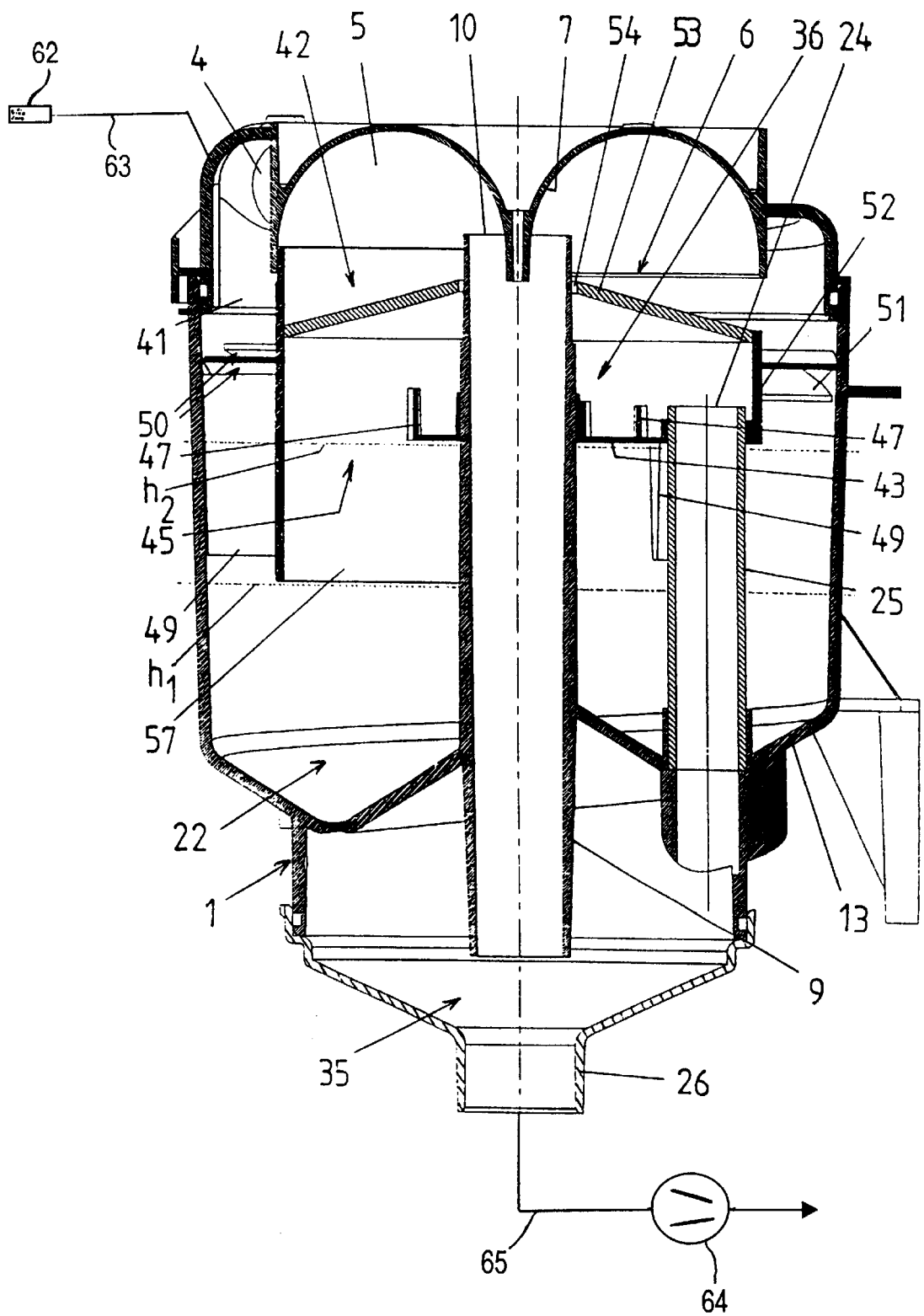
FIG. 2 is a longitudinal section through a second embodiment of the separator, taken along the line II—II of FIG. 3.

Referring now to FIG. 2, the second embodiment of the separator has a housing 1, which additionally has an air separation chamber 5 above the sedimentation tank 13, so that the aspirated air that entrains the mixture through the mixture inlet 4 into the separator is separated upstream of the solid separation, in the same apparatus. The air separation chamber 5 includes an apron-like deflection face 6 and a coupler-like deflection face 7 that is deep-drawn in the middle; the mixture inlet 4 is provided above and below the apron-like deflection face 6. The aspirated air is fed to an air outlet 10, which is provided on an upright tube 9 in the center of the sedimentation tank 13; the upper end of this tube is higher than the underside of the apron-like deflection face 6. The annular rib 52 joined to the bottom 43 of the insert element 42 has a baffle 59 which is drawn upward into the apron-like deflection face 6, over approximately half the circumference on both sides of the mixture inlet 4, in order to block the direct path to the air outlet 10 for the aspirated air. The mixture freed of the air leaves the air separation chamber 5 through a peripheral mixture outlet 41, extending all around the apron-like deflection face 6, and drops into the inlet chamber 50 located below this outlet; the inlet chamber is divided into a number of slit-like passages by obliquely placed laminations 51 ascending crosswise to the inflow direction. The radial edges of successive laminations 51 are each located virtually one above the other.

The insert element 42 in this embodiment, as FIG. 3 shows, has a third central opening 44, which is penetrated by the tube 9 that discharges below the sedimentation tank 13 into the outlet chamber 35, in which the separated air is reunited with the cleaned liquid. A line to a suction pump, embodied as a water ring pump and therefore also requiring the supply of liquid, is connected to the housing outlet 26 associated with the outlet chamber 35.

In order not to impede the sedimentation of the remaining solids, which are primarily fine, in the second sedimentation zone 36, this zone is shielded from the air separation chamber 5 with an approximately conical cover 53, which has a central opening 54 penetrated by the tube 9.

The sedimentation tank 13 can be removed from both the outlet chamber 35, forming a lower part of the housing 1, and the upper part of the housing 1 surrounding the air separation chamber 5, and once it is suitably filled with sedimented solids, it is replaced with an empty sedimentation tank 13.

Figure 4:
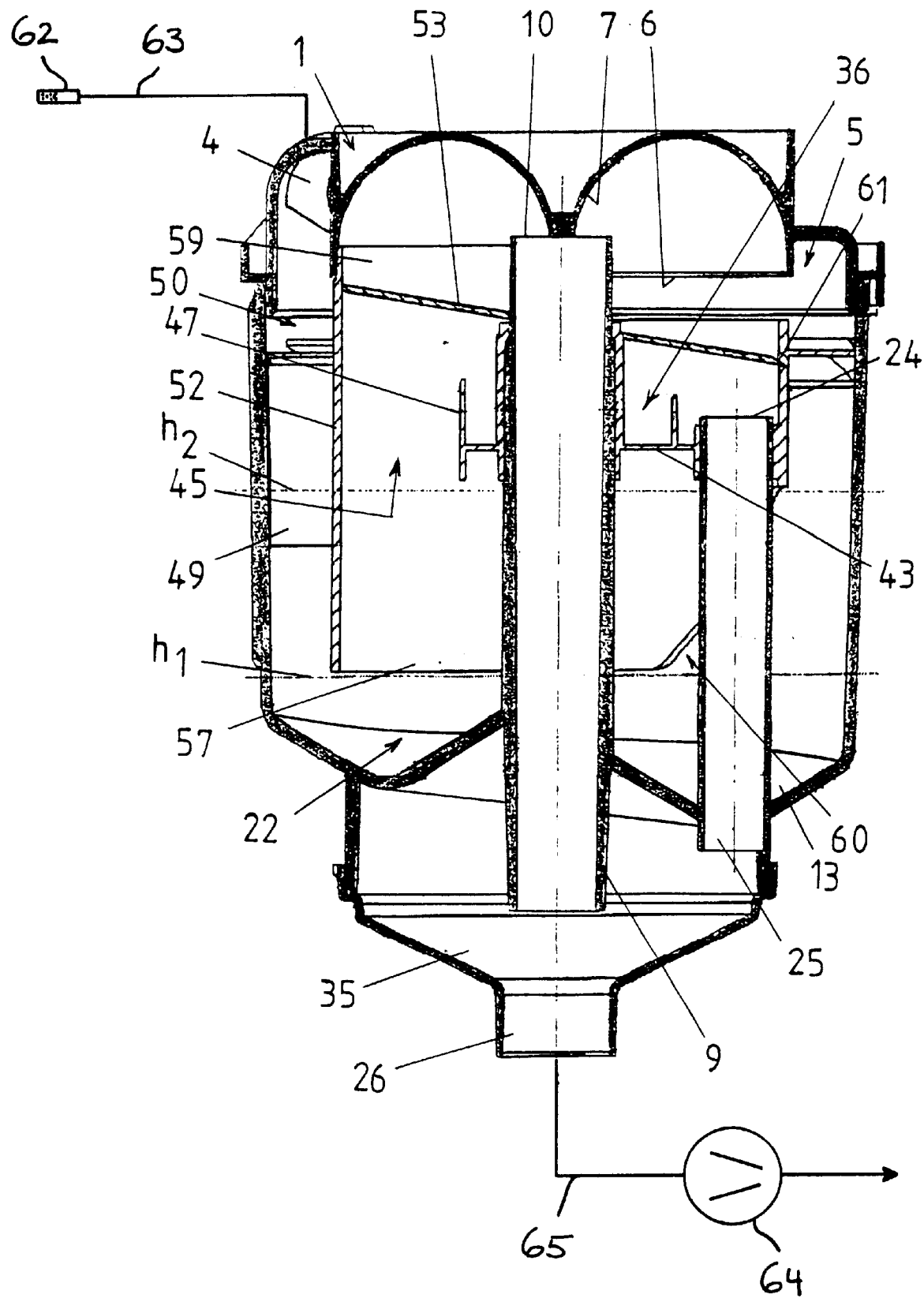
FIG. 4 is a longitudinal section through a third embodiment of the separator.

FIG. 4 shows a further embodiment of a separator with an air separation chamber 5 above the sedimentation tank 13; it differs from the embodiment of the FIG. 2 in some details that in particular lengthen the flow course through the first sedimentation zone 22.

For instance, the immersion wall 57 in comparison with FIG. 2 extends substantially farther downward into the sedimentation tank 13, and the lower edge extends horizontally over an angle of approximately 240 and comes to an obliquely ascending end. In other words, on the side opposite the mixture inlet 4, the immersion wall 57 has an approximately V-shaped cutout 60. As a result, once the direct flow course has grown shut, as soon as the sediment has reached the height $h_1$, the liquid must flow over a peripheral detour of at least 120, in order then through the V-shaped cut out 60 to reach the interior of the first sedimentation zone 22. The maximum sedimentation height $h_2$ is defined by the lower edge of the annular rib 52 in the region of the cutout 60.

The cover 53 of the second sedimentation zone 36 is also an inclined disk, at whose lowest point an opening 61 in the annular rib 52 enables the return flow into the inlet chamber 50 of any liquid that has collected on the cover 53 after having been separated from the deflected air.

There is also diagrammatically illustrated in FIG. 4 a suction nozzle 62 through which the air/solid/liquid mixture is aspirated from the mouth of a patient. The mixture is conducted through a suction line 63 which connects to the inlet opening 4 of the dental separator. The necessary suction is provided by a suction pump 64 which communicates with the suction line 63 "across" the separator. The suction pump 64 connects via a corresponding line 65 to the outlet 26 of the housing 1.

We claim:

1. A dental separator for separating out solids from a solid/liquid mixture after aspirated air has been separated off in a dental aspiration system, comprising:

a sedimentation tank for solids communicating fluidically with an upper inlet line and a lower wastewater conduit;

said sedimentation tank formed with a lower sedimentation zone and an upper sedimentation zone;

overflow ribs dividing said upper sedimentation zone into a plurality of chambers including a first chamber formed with an inlet opening communicating with said lower sedimentation zone and a last chamber formed with a liquid outlet; and a tube communicating with said liquid outlet formed in said last chamber and extending downward through said sedimentation tank towards the wastewater conduit;

wherein a flow path is defined through the dental separator from above into said lower sedimentation zone, into said upper sedimentation zone, over said overflow ribs to said last chamber, through said liquid outlet, and downward through said tube.

2. The separator according to claim 1, wherein said upper sedimentation zone is embodied in an insert element adapted to be inserted into said sedimentation tank, said insert element being formed with first and second bottom openings diametrically opposite one another and said overflow ribs disposed as mutually parallel overflow ribs therebetween, said first bottom opening fluidically connecting said lower sedimentation zone located below and said second bottom opening receiving said tube.

3. The separator according to claim 1, which further comprises an annular rib surrounding said upper sedimentation zone and forming, outside thereof, a peripheral inlet chamber communicating fluidically with said lower sedimentation zone.

4. The separator according to claim 3, which comprises an immersion wall protruding to various depths into said lower sedimentation zone and extending over a portion of a circumference of said annular rib.

5. In a dental aspiration system having a suction nozzle aspirating an air/solid/liquid mixture from a patient's mouth and a pump communicating with the suction nozzle via a suction line having a first portion and a second portion, a dental separator for separating the air/solid/liquid mixture connected to the suction nozzle via the first portion of said suction line and to the pump via the second portion of the suction line, the dental separator comprising:

a housing formed with an upper part, a middle part, and a lower part;

said upper part of said housing having an air separation chamber adapted to communicate fluidically with the first portion of the suction line and having deflection faces, and said air separation chamber having an air outlet and an outlet for the solid/liquid mixture;

said middle part of said housing having a sedimentation tank for solids disposed below said air separation chamber and communicating fluidically with said outlet for the solid/liquid mixture, said sedimentation tank being formed with a liquid outlet above a predetermined sedimentation height;

a plurality of overflow ribs disposed to divide said upper sedimentation zone into a plurality of chambers including a last chamber formed with said liquid outlet;

said lower part of said housing having an outlet chamber adapted to communicate fluidically with the second portion of the suction line and being disposed below said sedimentation tank; and said air outlet of said air separation chamber and said liquid outlet of said sedimentation tank communicating with said outlet chamber via a tube extending through said sedimentation tank and into said outlet chamber;

wherein a flow path through said housing is defined downward into said sedimentation tank and upwards to and through said liquid outlet.

6. The separator according to claim 5, wherein said air outlet and said liquid outlet are each provided via a respective tube discharging freely into said outlet chamber.

7. The separator according to claim 6, wherein said two tubes extend parallel to one another, and the tube of said air outlet is disposed centrally in said sedimentation tank, and the tube of said liquid outlet is disposed along a side wall of said sedimentation tank.

8. The separator according to claim 5, wherein said sedimentation tank forming said middle part of said housing is detachably joined to said upper part surrounding said air separation chamber and to said lower part formed with said outlet chamber.

9. The separator according to claim 5, wherein said second sedimentation zone is embodied in an insert element adapted to be inserted into said sedimentation tank and formed with first, second, and third bottom openings and mutually parallel overflow ribs, said second bottom opening being disposed diametrically opposite said first bottom opening and receiving said tube of said liquid outlet, and said tube of said air outlet extending through said third, central bottom opening.

10. The separator according to claim 5, which further comprises an annular rib surrounding said upper sedimentation zone and forming, outside thereof, a peripheral inlet chamber communicating fluidically with said outlet for the solid/liquid mixture.

11. The separator according to claim 10, which comprises an immersion wall protruding to various depths into said lower sedimentation zone and extending over a portion of a circumference of said annular rib.

12. The separator according to claim 10, which comprises laminations ascending crosswise to an inflow direction disposed in said inlet chamber adjacent said ribs, said laminations having mutually spaced apart radial edges and being disposed one above the other.

13. The separator according to claim 10, which comprises a cover of said second sedimentation zone inside said annular rib, said cover being formed with a center opening penetrated by said tube of said air outlet.

* * * * *